United States Patent [19]
Smith

[11] Patent Number: 5,256,063
[45] Date of Patent: Oct. 26, 1993

[54] DENTAL RETENTION PIN FOR PICK-UP MODELS AND IMPRESSION POURING

[76] Inventor: Avis J. Smith, 380 Cozine Ave., #4A, Brooklyn, N.Y. 11207

[21] Appl. No.: 982,458

[22] Filed: Nov. 27, 1992

[51] Int. Cl.$^5$ .......................... A61C 19/00; A61C 5/08
[52] U.S. Cl. ........................................ 433/74; 433/221
[58] Field of Search ................... 433/74, 220, 221, 225

[56] References Cited

U.S. PATENT DOCUMENTS

| | | | |
|---|---|---|---|
| 2,536,669 | 1/1951 | Thau-Jensen | 433/221 |
| 3,226,827 | 1/1966 | Spalten | 433/74 X |
| 4,054,995 | 10/1977 | Yoshida | 433/74 |
| 4,443,192 | 4/1984 | Blitz | 433/74 |
| 4,752,225 | 6/1988 | Bori | 433/221 |
| 5,073,112 | 12/1991 | Weil | 433/220 X |
| 5,161,973 | 11/1992 | Johnson | 433/221 |
| 5,178,540 | 1/1993 | Noone | 433/220 |

FOREIGN PATENT DOCUMENTS

| | | | |
|---|---|---|---|
| 2553282 | 4/1985 | France | 433/225 |
| 2210792 | 6/1989 | United Kingdom | 433/225 |

*Primary Examiner*—Gene Mancene
*Assistant Examiner*—Nicholas D. Lucchesi
*Attorney, Agent, or Firm*—Charles E. Baxley

[57] ABSTRACT

A one-piece dental retention pin is symmetrical with respect to a central plane and has an upper end and a lower end and parallel first and second face surfaces. The pin has a top portion extending from the upper end toward the lower end and a bottom portion extending from the lower end to a location of juncture with the top portion and tapering from a location of minimum width at the lower end to a location of maximum width about halfway between the lower end and the juncture of the bottom portion and the top portion and then tapers to diminish in width to its location of juncture with the top portion. A central hole therethrough joins the face surfaces which have serrations in the bottom portion.

3 Claims, 1 Drawing Sheet

DENTAL RETENTION PIN FOR PICK-UP MODELS AND IMPRESSION POURING

BACKGROUND OF THE INVENTION

This invention relates to dentistry and more particularly to a dental retention pin for use in pick-up models and/or impression pouring, more particularly two-step impression pouring.

The invention presents a retention pin that is simplified with respect to prior art devices presently in use. Furthermore, the retention pin of the invention is extremely simple to use, and one disclosed embodiment of the invention is suitable for use with removable dies.

SUMMARY OF THE INVENTION

The invention provides a one-piece dental retention pin that is symmetrical with respect to a central plane and having an upper end and a lower end and parallel first and second face surfaces. The pin has a top portion extending from the upper end toward the lower end and a bottom portion extending from the lower end to a location of juncture with the top portion and tapering from a location of minimum width at the lower end to a location of maximum width about halfway between the lower end and the juncture of the bottom portion and the top portion and then tapers to diminish in width to its location of juncture with the top portion and having a central hole therethrough ending at the face surfaces, and the face surfaces have serrations in the bottom portion.

DESCRIPTION OF THE INVENTION

Figure 1:
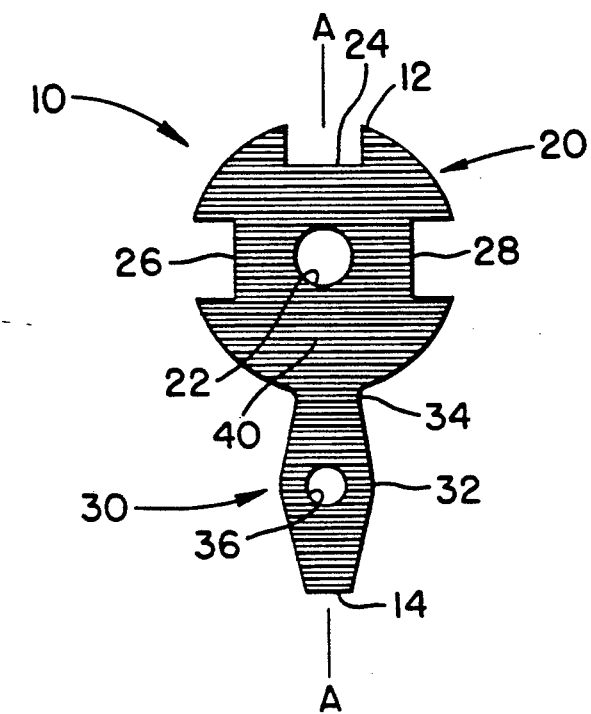
FIG. 1 is a front (or rear) elevation of a retention pin that is a first preferred embodiment of the invention.
Figure 2:
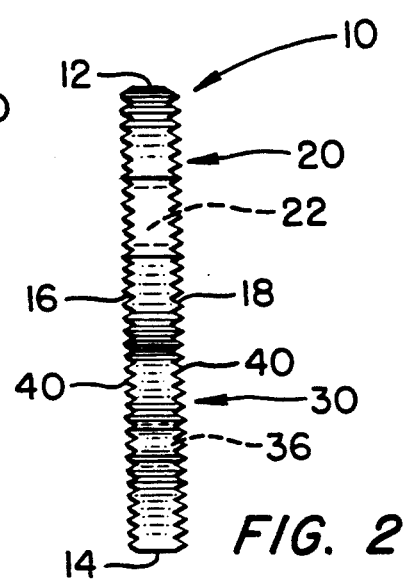
FIG. 2 is a side (right or left) view of the retention pin of FIG. 1.

FIGS. 1 and 2 illustrate a dental retention pin 10 that is a first preferred embodiment of the invention. More particularly, FIG. 1 is a front (or rear) elevation of pin 10 while FIG. 2 is a side (right or left) view of pin 10. Pin 10 is of one-piece molded plastic material and is symmetrical with respect to a central plane designated A—A that is perpendicular to the paper in FIG. 1.

Pin 10 extends from an upper end 12 to a lower end 14 and from a first face surface 16 to a second face surface 18. Face surfaces 16 and 18 are parallel to each other and either can be considered a front surface or a rear surface. The length of pin 10 from upper end 12 to lower end 14 may be about 0.75 inch (1.9 cm) and the thickness of pin 10 from face surface 16 to face surface 18 may be on the order of 0.125 inch (0.32 cm).

Pin 10 has a top portion 20 which extends about halfway from upper end 12 toward lower end 14 and which is of generally circular outline. Top portion 20 has a central hole 22 there-through, centered on plane A—A, and like undercut external recesses 24, 26 and 28 facing away from hole 22. Recess 24 is centered on plane A—A at upper end 12 and recesses 26 and 28 are spaced 180 degrees from each other, each 90 degrees from recess 24.

Pin 10 further has a bottom or stem portion 30 extending from lower end 14 to a location of juncture with top portion 20, about midway between upper end 12 and lower end 14. Bottom or stem portion 30 tapers from a location of minimum width at lower end 14 to a location 32 of maximum width about halfway between lower end 14 and the juncture of bottom portion 30 and top portion 20 and then tapers to diminish in width to its location of juncture 34 with top portion 20. Bottom portion 30 also has a hole 36 therethrough, centered on plane A—A at location 32 of maximum width.

Face surfaces 16 and 18 of pin 12 are provided with serrations as indicated at 40, generally perpendicular to plane A—A.

Figure 3:
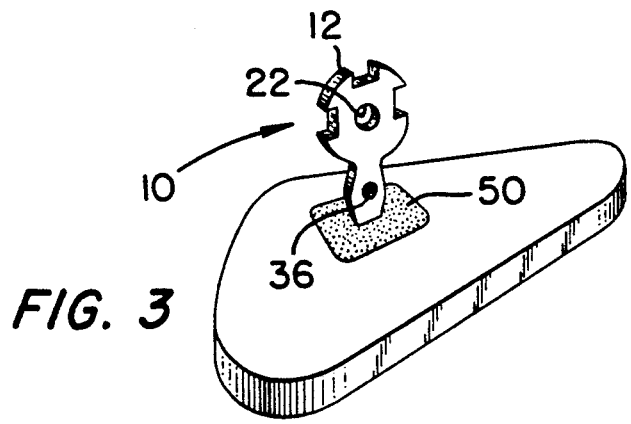
FIG. 3 is a fragmentary perspective, somewhat schematic view showing the retention pin of FIG. 1 in the process of being inserted in a poured cast.

FIG. 3 shows a poured cast 50 with pin 10 being inserted therein.

In result, holes 22 and 36, undercut external recesses 24, 26 and 28, serrations 40 and the tapered configuration of bottom portion 30 cooperate to provide superior retention and immobilization of pin 10 in the crown area and the poured cast.

Figure 4:
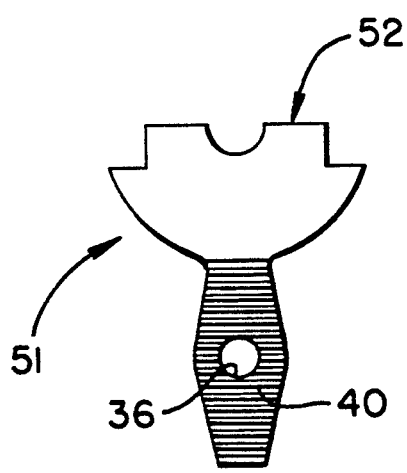
FIG. 4 is a front (or rear) elevation of a retention pin that is a second preferred embodiment of the invention.
Figure 5:
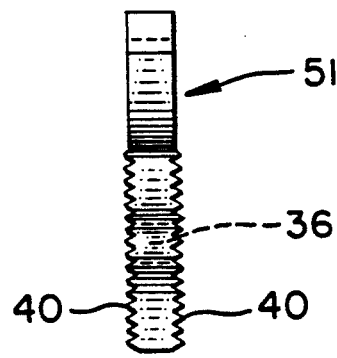
FIG. 5 is a side (right or left) view of the retention pin of FIG. 4.

FIGS. 4 and 5 show a retention pin 50 that is a second preferred embodiment of the invention. Pin 50 is similar to pin 10 except that pin 50 has a top portion 52 that is modified to remove the part of top portion 20 located above the center of hole 22 and to remove serrations 40 from the remaining half of top portion 52. Pin 50 is suitable for use with removable dies.

It is apparent that the invention well attains the stated objects and advantages, among others.

The disclosed details are exemplary only and are not to be taken as limitations on the invention except as those details are included in the appended claims.

What is claimed is:

1. A one-piece dental retention pin that is symmetrical with respect to a central plane and having an upper end and a lower end and parallel first and second face surfaces, said pin having a top portion extending from said upper end toward said lower end and a bottom portion extending from said lower end to a location of juncture with said top portion and tapering from a location of minimum width at said lower end to a location of maximum width about half way between said lower end and the juncture of said bottom portion and said top portion and then tapering to diminish in width at its location of juncture with said top portion and having a central hole therethrough joining said face surfaces, and said face surfaces having serrations along said bottom portion, wherein said top portion extends about halfway from said upper end towards said lower end and is of generally circular outline, said top portion having a central hole therethrough and like undercut external recesses facing away from said last mentioned hole.

2. The pin of claim 1 wherein said undercut external recesses are three in number, a first of said recesses being centered on said central plane at said upper end, and a second and a third of said recesses being spaced 180 degrees from each other and 90 degrees from said first recess.

3. The pin of claim 2 wherein the entirety of each of said face surfaces is serrated.

* * * * *